United States Patent [19]
Akhter et al.

[11] Patent Number: 5,383,474
[45] Date of Patent: Jan. 24, 1995

[54] APPARATUS FOR STUDYING THE EFFECTS OF COMPRESSIVE AND TENSILE BENDING STRAINS ON BONES

[75] Inventors: Mohammed P. Akhter; Robert R. Recker, both of Omaha, Nebr.

[73] Assignee: Creighton University Office of Technology Licensing, Omaha, Nebr.

[21] Appl. No.: 134,446

[22] Filed: Oct. 12, 1993

[51] Int. Cl.6 .............................................. A61B 5/103
[52] U.S. Cl. ..................................................... 128/782
[58] Field of Search ......................... 128/774, 779, 782

[56] References Cited

U.S. PATENT DOCUMENTS

| | | | |
|---|---|---|---|
| 4,583,555 | 4/1986 | Malcom et al. | 128/782 |
| 4,799,497 | 1/1989 | Riley | 128/782 |
| 4,969,471 | 11/1990 | Daniel et al. | 128/782 |

FOREIGN PATENT DOCUMENTS 0324279  7/1989  European Pat. Off. ............. 128/774

OTHER PUBLICATIONS

Young et al. "In-Vivo Bone Strain Telemetry in Monkeys" Jrl. of Biomech. Eng. May 1977.

Primary Examiner—Max Hindenburg
Attorney, Agent, or Firm—Suiter & Associates; Sean Patrick Suiter

[57] ABSTRACT

An apparatus for applying compressive and tensile loads on bones having a frame with a work surface and a stepper motor. The stepper motor is operably connected to a rotational force to linear force converter which is in turn connected to an articulating arm for applying force to a first pair of pads. A second pair of pads is mounted to the work surface such that a bone may be placed across the second pair of pads such that either end of the bone is supported by the second pair of pads and such that the activation of the stepper motor causes the upper pair of pads to exert compressive bending strain on the lateral surface of the bone and such that the lower pair of pads exert tensile bending strain on the medial surface of the bone. A method of modifying hard tissue morphology is also described.

1 Claim, 2 Drawing Sheets

APPARATUS FOR STUDYING THE EFFECTS OF COMPRESSIVE AND TENSILE BENDING STRAINS ON BONES

GOVERNMENT RIGHTS

The present invention was partially funded by a grant from the United States government.

SPECIFICATION

Authorization Pursuant to 37 C.F.R. 1.71(d) and (e)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS REFERENCES

Related Applications

The present application is an original patent application.

TECHNICAL FIELD

The present invention is generally related to load applying apparatus and more particularly to a novel method and apparatus for studying the effects of imparting controlled compressive and tensile loads on bones.

BACKGROUND ART

The in vivo bone response to mechanical stimulus is not well defined. In order to determine and analyze the response an apparatus and method for inducing the stimulus is necessary. Unfortunately, heretofore, neither a suitable method nor apparatus was available for studying the short and long term effects of such stimulus. The morphology of hard tissue exposed to mechanical stimulus may best be determined via a quantifiable method of applying both compressive and tensile forces to hard tissue.

DISCLOSURE OF INVENTION

The apparatus of the present invention provides a method of applying compressive and tensile loads on bones. The apparatus of an exemplary embodiment includes a frame with a work surface and a stepper motor. The stepper motor is operably connected to a rotational-force-to-linear-force converter which is in turn connected to an articulating arm for applying force to an upper pair of pads. A lower pair of pads is mounted to the work surface such that the bone of an animal may be placed across the lower pair of pads such that either end of an animal bone is supported by the lower pair of pads, and such that the activation of the stepper motor causes the upper pair of pads to exert compressive bending strain on the lateral surface and the lower pair of pads exert tensile bending strain on the medial surface of the bone such that the apparatus may be utilized to cause both tensile and compressive loads. A method of modifying hard tissue morphology is also described.

MODES FOR CARRYING OUT THE INVENTION

The present invention 10 teaches a novel apparatus for studying the effects of controlled bone exercise. The apparatus 10 may be used in an exemplary embodiment, to study the in viva bone (12) response to mechanical stimulus (bending strain).

Figure 1:
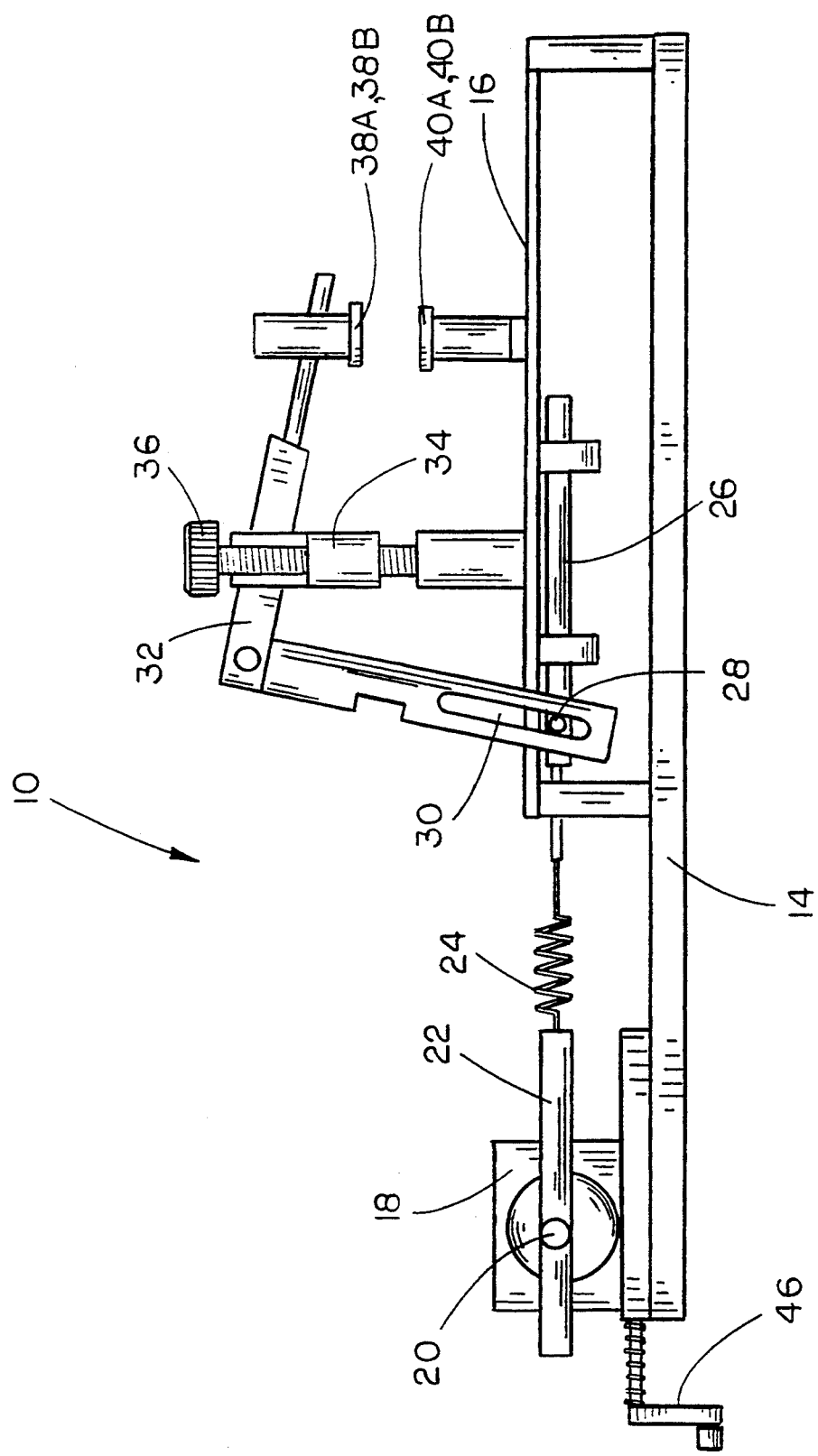
FIG. 1 is a side elevation of the present invention illustrating the primary components of a preferred embodiment.
Figure 2A:
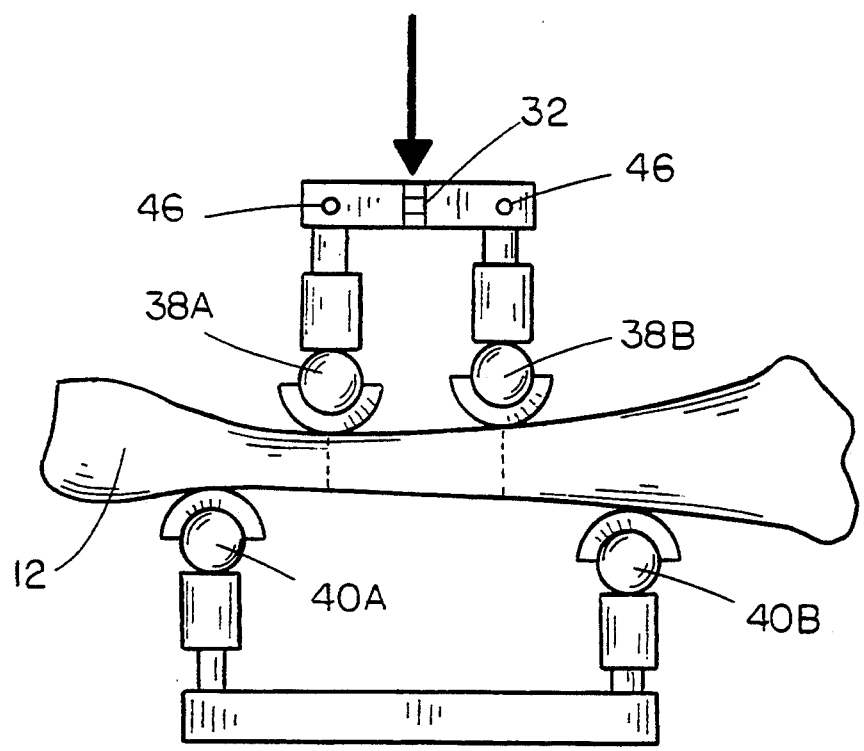
FIGS. 2A and 2B are partial front elevational views illustrating an exemplary apparatus for utilizing the invention according to a preferred method.

By turning first to FIG. 1, wherein the major components of an exemplary embodiment are illustrated, the operation of the apparatus 10 will become known. In a preferred embodiment a frame 14 having an upstanding flat work surface 16 is provided. A stepper motor and programmable controller 18 operable at 200 steps per revolution (available from Superior Electronics, Bristol, Conn.) is mounted to the frame 14. The drive shaft 20 of the motor is operably connected to a force converter 22 The converter 22 (rotating arm) is adapted to convert the rotational energy of the motor to linear energy. The converter 22 is connected to a spring 24 which is in turn connected to a slide bar 26 (slidably mounted on the undersurface of the work surface 16). Pivotably connected to the slide bar 26 (via a pin 28 [slide bar pin] and slot 30 [lever arm]) is a lever arm strain gauge 32. The lever arm 32 is adjustably and pivotably connected to the work surface 16 via a lever arm support 34. An adjustment screw 36 is provided in the support 34 for adjusting the height of a first pair of loading pads (38A, 38B) (see FIGS. 2A and 2B).

Figure 2B:
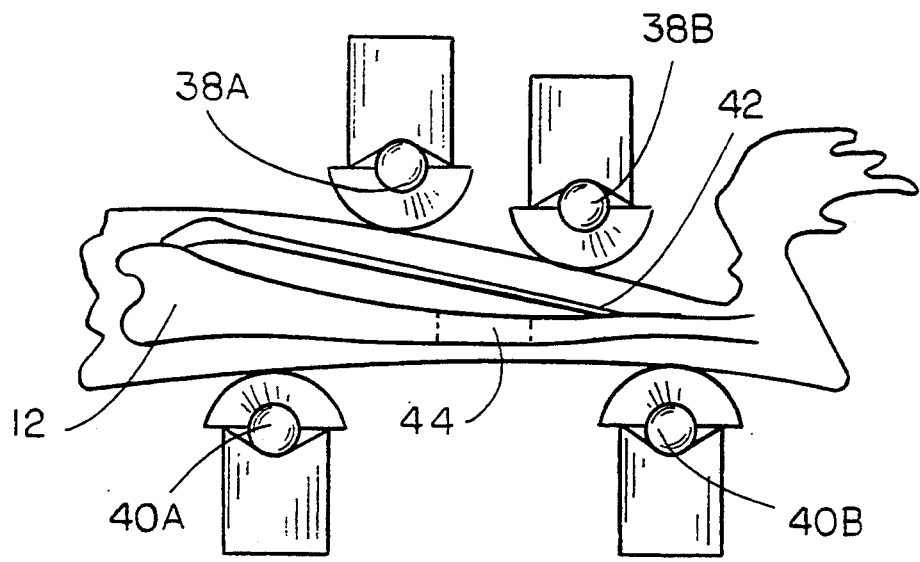

Mounted on the work surface is a lower pair of coacting loading pads (40A, 40B). The lower pair of pads is mounted 23 mm apart and the upper pair of pads is mounted 11 mm apart (in an embodiment adapted to study the effect of mechanical stimulus on rat tibia). The upper pair of loading pads (38A, 38B) are pivotally mounted (46) (FIG. 2A) such that both pads are maintained in contact with the soft tissue surrounding the bone to be loaded. According to a preferred method the upper pair of loading pads is set such that one of the pads applies force just ahead of the tibio-fibula junction 42 and such that an undisturbed loading zone 44 of approximately 8.5 mm is produced in the rat tibia (FIG. 2B). By activating the stepper motor and programmable controller 18 the upper loading pads produce a compressive bending strain on the lateral surface of the rat tibia and the lower loading pads produce a tensile bending strain on the medial surface of the rat tibia.

In accordance with a preferred method the apparatus 10 is utilized to (1) induce precise and unique (non-physiologic bending) loads on rat tibia and (2) to provide a method of studying the bone response to the controlled loading. The apparatus 10 has been utilized to induce bending strain to the right tibia of rats (average weight 330 g). The apparatus 10 utilizes the programmable stepper motor 18 to control the frequency and number of loading cycles. In an exemplary embodiment the apparatus 10 may be set to deliver load levels at intervals of 5N. Whereas the specific materials from which the apparatus is formed is not critical to the invention, the apparatus of the exemplary embodiment was manufactured from aluminum and the bending load is imparted via four loading pads fabricated from surgical tubing (surgical tubing was utilized so as to better distribute the load while also minimizing soft tissue injury).

As may be seen (FIG. 1) the apparatus of an exemplary embodiment utilizes a lever system which converts and magnifies horizontal axis linear displacement to vertical axis linear displacement. In a preferred embodiment the lever arm is equipped with a strain gauge 50 (available from Micro Measurements Group, Raleigh, N.C.). Such a gauge may be utilized to monitor load delivery. In an exemplary embodiment there are five settings on the motor arm which may be utilized to selectively impart 40, 35, 30, 25, and 20N loads. The load frequency (or load rate) is controlled via the stepper motor controller.

Whereas the invention has been shown and described in connection with a preferred embodiment thereof, it is apparent that many additions, modifications and substitutions may be made which are within the intended broad scope of the appended claims. For example, different linkages might be employed to impart the four point load. Thus, there has been shown and described an apparatus for applying compressive and tensile bending loads to bones and a method for utilizing the same.

We claim:

1. An apparatus for applying compressive and tensil bending loads on bones comprising:

(a) a frame having a work surface;

(b) driving means for producing rotational force at controllable frequencies mounted to said frame;

(c) conversion means connected to said driving means for converting rotational force to linear force;

(d) articulating arm means having a first end operably connected to said conversion means and a second end pivotably connected to at least a pair of upper pads, each member of the pair of said upper pads being spaced at a sufficient distance from the other member of the pair so that the two members of the pair of said pads provide contact at distinct points on the upper lateral surface of an animal bone located below said upper pair of pads;

(e) at least a pair of lower pads mounted on said work surface such that an animal bone may be placed across and supported by said lower pair of pads at points between the distal and proximal bone ends, each member of the said lower pair of pads being spaced at a sufficient distance from the other member such that the points of contact between the lower surface of the said bone and the members of said lower pads are closer to the proximal and distal ends of the bone than the points of contact between the upper surface of the bone and the members of said upper pair of pads; whereby, activation of the said driving force causes said upper pair of pads to exert compressive bending strain on the lateral surface of said bone and simultaneously causes said lower pair of pads to exert tensile bending strain on the medial surface of said bone.

* * * * *